United States Patent
Dickinson et al.

(10) Patent No.: US 8,404,218 B2
(45) Date of Patent: *Mar. 26, 2013

(54) GELLED WATER-IN-OIL MICROEMULSIONS FOR HAIR TREATMENT

(75) Inventors: Kelvin Brian Dickinson, Wirral (GB); Anand Ramchandra Mahadeshwar, Hamburg (DE); Ruby Loo Bick Tan-Walker, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 1397 days.

This patent is subject to a terminal disclaimer.

(21) Appl. No.: 11/793,906

(22) PCT Filed: Nov. 11, 2005

(86) PCT No.: PCT/EP2005/012228
§ 371 (c)(1),
(2), (4) Date: Mar. 11, 2008

(87) PCT Pub. No.: WO2006/066668
PCT Pub. Date: Jun. 29, 2006

(65) Prior Publication Data
US 2011/0177019 A1 Jul. 21, 2011

(30) Foreign Application Priority Data
Dec. 23, 2004 (EP) .................... 04258088

(51) Int. Cl.
*A61K 8/00* (2006.01)
*A61Q 5/02* (2006.01)
(52) U.S. Cl. ...................... 424/70.1; 424/401

(58) Field of Classification Search .................. None
See application file for complete search history.

(56) References Cited

U.S. PATENT DOCUMENTS

| | | | |
|---|---|---|---|
| 4,940,577 A | * | 7/1990 | Greenberg et al. ............. 424/59 |
| 5,298,240 A | * | 3/1994 | Schroder et al. ........... 424/70.19 |
| 6,579,907 B1 | | 6/2003 | Sebillotte-Arnaud et al. ............. 514/772.4 |
| 6,607,733 B1 | | 8/2003 | Diec et al. ..................... 424/401 |

(Continued)

FOREIGN PATENT DOCUMENTS

| | | |
|---|---|---|
| DE | 44 11 557 | 10/1995 |
| EP | 0 247 552 | * 12/1987 |

(Continued)

OTHER PUBLICATIONS

PCT International Search Report in a PCT application PCT/EP2005/012228, Jan. 27, 2006.

(Continued)

*Primary Examiner* — Lakshmi Channavajjala
(74) *Attorney, Agent, or Firm* — Ronald A. Koatz

(57) ABSTRACT

The present invention provides a gelled water-in-oil microemulsion for hair treatment comprising: (a) an oil phase comprising: (i) a first oily component which is one or more glyceride fatty esters, and (ii) a second oily component which is one or more hydrocarbon oils of average carbon chain length less than 20 carbon atoms; (b) a hydrophilic phase comprising: (i) water, (ii) a nonionic emulsifier which is an ethoxylated alcohol having an HLB of at least 6, and (iii) preferably, a hair styling agent or hair conditioning agent, and (c) a gelling agent.

14 Claims, 1 Drawing Sheet

U.S. PATENT DOCUMENTS

| | | | |
|---|---|---|---|
| 2002/0039564 A1* | 4/2002 | Dickinson et al. | 424/70.1 |
| 2002/0159961 A1* | 10/2002 | Yamato et al. | 424/65 |
| 2004/0115155 A1* | 6/2004 | Salvador et al. | 424/70.13 |
| 2004/0166074 A1 | 8/2004 | Darkwa et al. | 424/70.1 |
| 2005/0232953 A1* | 10/2005 | Barnikol et al. | 424/400 |
| 2008/0311062 A1* | 12/2008 | Dickinson et al. | 424/70.1 |
| 2009/0098078 A1* | 4/2009 | Dickinson et al. | 424/70.11 |

FOREIGN PATENT DOCUMENTS

| | | |
|---|---|---|
| EP | 0 490 053 | 8/1994 |
| EP | 1 269 974 | 1/2003 |
| EP | 1 417 951 | 5/2004 |
| EP | 1 289 479 | 11/2006 |
| WO | 95/23581 | 9/1995 |
| WO | 00/61084 | 10/2000 |
| WO | 01/45651 | 6/2001 |
| WO | WO 01/45651 * | 6/2001 |
| WO | 2006/066656 | 6/2006 |
| WO | 2006/066703 | 6/2006 |
| WO | 2006/066710 | 6/2006 |

OTHER PUBLICATIONS

PCT International Search Report in a PCT application PCT/EP2005/011973, Jan 27, 2006.
PCT International Search Report in a PCT application PCT/EP2005/012849, Jan. 27, 2006.
PCT International Search Report in a PCT application PCT/EP2005/012907, Feb. 1, 2006.
Derwent Abstract of DE 44 11 557—published Oct. 5, 1995.
Derwent Abstract of EP 0 490 053—published Aug. 3, 1994.
Japanese Abstract JP 08 268829—published Oct. 15, 1996.
Japanese Abstract JP 63 126542—published May 30, 1988.
Japanese Abstract JP 11 171737—published Jun. 29, 1999.
Japanese Abstract JP 11 286420—published Oct. 19, 1999.
Derwent Abstract of EP 1 417 951 published May 12, 2004.

* cited by examiner

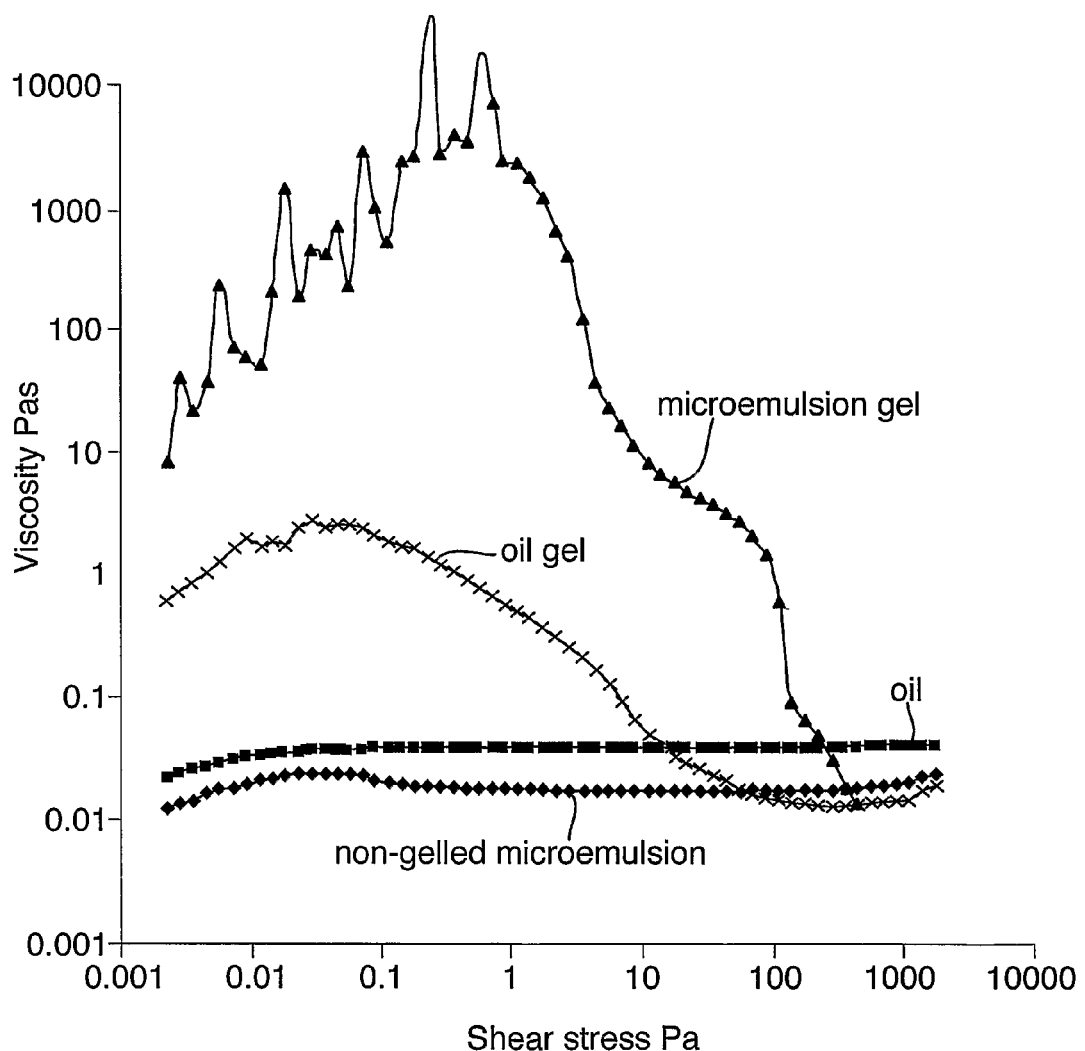

GELLED WATER-IN-OIL MICROEMULSIONS FOR HAIR TREATMENT

FIELD OF THE INVENTION

This invention relates to gelled water-in-oil microemulsions for hair treatment which have enhanced rheology, sensory properties and compatibility with hair benefit agents.

BACKGROUND OF INVENTION AND PRIOR ART

Consumers oil hair both pre wash and post wash. Pre wash oiling is done as it is believed that oils nourish hair and protect it during the wash process. Post wash oiling is done for manageability and styling. The oiling habit is widely practised by around 800 million people across the Central Asia and Middle East region.

Coconut oil is by far the most common oil used in the Central Asia and Middle East region for hair care. It offers a high level of conditioning benefits, but with the drawback of greasy feel.

EP 1289479 discloses hair oils which incorporate a specific blend of oil types (glyceride fatty esters and hydrocarbon oils) and which can deliver an equivalent level of conditioning benefits to coconut oil, but with superior sensory properties, in particular less greasy feel.

The oil should be easily applied or spread onto the hair by brush or fingers to provide uniform coverage of the oil throughout the hair. However, once applied it should not drip or run off the hair. It would be desirable to incorporate a rheology modifier such as a gelling agent into the oil in order to improve these properties, but a problem is that the incorporation of gelling agent into the oil at a sufficient level to give the desired product rheology can result in sensory negatives such as a sticky, greasy feel.

The present inventors have found that this problem can be solved if the gelling agent is incorporated into a water-in-oil microemulsion formed with a particular type of nonionic emulsifier. The gel so obtained exhibits enhanced viscosity and shear-thinning properties, yet without sensory negatives such as a sticky, greasy feel. Advantageously, it also exhibits enhanced compatibility with hair benefit agents such as hair styling agents and hair conditioning agents (which are normally incompatible with oils).

DEFINITION OF THE INVENTION

The present invention provides a gelled water-in-oil microemulsion for hair treatment comprising:
(a) an oil phase comprising:
(i) a first oily component which is one or more glyceride fatty esters, and
(ii) a second oily component which is one or more hydrocarbon oils of average carbon chain length less than 20 carbon atoms;
(b) a hydrophilic phase comprising:
(i) water,
(ii) a nonionic emulsifier which is an ethoxylated alcohol having an HLB of at least 6, and
(iii) preferably, a hair styling agent or hair conditioning agent, and
(c) a gelling agent.

DETAILED DESCRIPTION OF THE INVENTION

Microemulsion

By "microemulsion" is meant a thermodynamically or kinetically stable liquid dispersion of an oil phase and a hydrophilic phase. The dispersed phase typically comprises small particles or droplets, with a size range of 5 nm to 200 nm, giving rise to a microemulsion that is transparent or translucent in appearance. This is in contrast to regular (macro-) emulsions that are turbid. The droplets or particles of the microemulsion may be spherical, although other structures are possible. The microemulsion is formed readily and sometimes spontaneously, generally without high-energy input.

(a)(i) Glyceride Fatty Ester

The gelled water-in-oil microemulsion of the invention comprises an oil phase comprising a first oily component which is one or more glyceride fatty esters.

By "glyceride fatty esters" is meant the mono-, di-, and tri-esters formed between glycerol and long chain carboxylic acids such as $C_6$-$C_{30}$ carboxylic acids. The carboxylic acids may be saturated or unsaturated or contain hydrophilic groups such as hydroxyl.

Preferred glyceride fatty esters are derived from carboxylic acids of carbon chain length ranging from $C_6$ to $C_{24}$, preferably $C_{10}$ to $C_{22}$, most preferably $C_{12}$ to $C_{18}$.

Suitable glyceride fatty esters for use in gelled microemulsions of the invention will generally have a viscosity at ambient temperature (25 to 30° C.) of from 0.01 to 0.8 Pa·s, preferably from 0.015 to 0.6 Pa·s, more preferably from 0.02 to 0.065 Pa·s as measured by a Carri-Med CSL2 100 controlled stress rheometer, from TA Instruments Inc., New Castle, Del. (USA).

A variety of these types of materials are present in vegetable and animal fats and oils, such as camellia oil, coconut oil, castor oil, safflower oil, sunflower oil, peanut oil, cottonseed oil, corn oil, olive oil, cod liver oil, almond oil, avocado oil, palm oil, sesame oil, lanolin and soybean oil. These have various ranges of carbon chain lengths depending on the source, typically between about 12 to about 18 carbon atoms. Synthetic oils include trimyristin, triolein and tristearin glyceryl dilaurate. Vegetable derived glyceride fatty esters are particularly preferred, and specific examples of preferred materials for inclusion in gelled microemulsions of the invention as sources of glyceride fatty esters include almond oil, castor oil, coconut oil, sesame oil, sunflower oil and soybean oil. Coconut oil, sunflower oil, almond oil and mixtures thereof are particularly preferred.

The glyceride fatty ester may be present in gelled microemulsions of the invention as a single material or as a blend.

The total content of glyceride fatty ester in gelled microemulsions of the invention suitably ranges from 10% to 95%, preferably from 20% to 80%, by weight based on total weight of the gelled microemulsion.

(a)(ii) Hydrocarbon Oil

The oil phase of the gelled water-in-oil microemulsion of the invention comprises a second oily component which is one or more hydrocarbon oils of average carbon chain length less than 20 carbon atoms.

Suitable hydrocarbon oils include cyclic hydrocarbons, straight chain aliphatic hydrocarbons (saturated or unsaturated), and branched chain aliphatic hydrocarbons (saturated or unsaturated). Straight chain hydrocarbon oils will typically contain from about 6 to about 16 carbon atoms, preferably from about 8 up to about 14 carbon atoms. Branched chain hydrocarbon oils can and typically may contain higher numbers of carbon atoms, e.g. from about 6 up to about 20 carbon atoms, preferably from about 8 up to about 18 carbon atoms.

Suitable hydrocarbon oils will generally have a viscosity at ambient temperature (25 to 30° C.) of from 0.0001 to 0.5 Pa·s, preferably from 0.001 to 0.05 Pa·s, more preferably from 0.001 to 0.02 Pa·s as measured by a Carri-Med CSL2 100 controlled stress rheometer, from TA Instruments Inc., New Castle, Del. (USA).

A preferred hydrocarbon oil is light mineral oil. Mineral oils are clear oily liquids obtained from petroleum oil, from which waxes have been removed, and the more volatile fractions removed by distillation. The fraction distilling between 250° C. to 300° C. is termed mineral oil, and it consists of a mixture of hydrocarbons, in which the number of carbon atoms per hydrocarbon molecule generally ranges from $C_{10}$ to $C_{40}$. Mineral oil may be characterised in terms of its viscosity, where light mineral oil is relatively less viscous than heavy mineral oil, and these terms are defined more specifically in the U.S. Pharmacopoeia, 22nd revision, p. 899 (1990). A commercially available example of a suitable light mineral oil for use in the invention is Sirius M40 (carbon chain length $C_{10}$-$C_{28}$, mainly $C_{12}$-$C_{20}$, viscosity $4.3 \times 10^{-3}$ Pa·s), available from Silkolene.

Other hydrocarbon oils that may be used in the invention include relatively lower molecular weight hydrocarbons including linear saturated hydrocarbons such a tetradecane, hexadecane, and octadecane, cyclic hydrocarbons such as dioctylcyclohexane (e.g. CETIOL S from Henkel), branched chain hydrocarbons (e.g. ISOPAR L and ISOPAR V from Exxon Corp.).

The hydrocarbon oil may be present in gelled microemulsions of the invention as a single material or as a blend.

The total content of hydrocarbon oil in gelled microemulsions of the invention suitably ranges from 5% to 90%, preferably from 20% to 80%, by weight based on total weight of the gelled microemulsion.

The glyceride fatty ester:hydrocarbon oil weight ratio in gelled microemulsions of the invention may suitably range from 90:10 to 10:90, preferably from 80:20 to 20:80, more preferably from 60:40 to 40:60. Particularly preferred are blends of [coconut oil and/or sunflower oil and/or almond oil] and light mineral oil, in which the [coconut oil and/or sunflower oil and/or almond oil]:light mineral oil weight ratio is about 50:50.

(b)(i) Water

The hydrophilic phase of the gelled water-in-oil microemulsion of the invention comprises water, suitably at a level of from about 2% by weight based on total weight of the gelled microemulsion. Suitably the water level does not exceed about 10% by weight based on total weight of the gelled microemulsion, since this may lead to a hazy product appearance which is undesirable to consumers of hair oils. Preferably the water level ranges from 3 to 7%, more preferably from 4 to 6% by weight based on total weight of the gelled microemulsion.

(b)(ii) Nonionic Emulsifier

The gelled water-in-oil microemulsion of the invention comprises a nonionic emulsifier which is an ethoxylated alcohol having an HLB of at least 6.

Suitable ethoxylated alcohols are commercially available and include the primary aliphatic alcohol ethoxylates and secondary aliphatic alcohol ethoxylates. The length of the polyethenoxy chain can be adjusted to achieve the desired balance between the hydrophobic and hydrophilic elements.

The HLB value of the ethoxylated alcohol suitably ranges from 6 to 12, preferably from 7 to 10, more preferably from 7 to 9.

Examples of suitable ethoxylated alcohols include the condensation products of a higher alcohol (e.g., an alkanol containing about 8 to 16 carbon atoms in a straight or branched chain configuration) condensed with about 2.5 to 20 moles of ethylene oxide.

A preferred group of the foregoing ethoxylated alcohols are the Neodol ethoxylates (Shell Co.), which are higher aliphatic, primary alcohols containing about 9 to 15 carbon atoms condensed with about 2.5 to 20 moles of ethylene oxide. Specific examples are C9 to 11 alkanol condensed with 2.5 to 10 moles of ethylene oxide (Neodol 91-8 or Neodol 91-5), C12 to 13 alkanol condensed with 3 moles ethylene oxide (Neodol 23-3), C12 to 15 alkanol condensed with 12 moles ethylene oxide (Neodol 25-12), C14 to 15 alkanol condensed with 13 moles ethylene oxide (Neodol 45-13), and the like. Such ethoxylates have an HLB (hydrophobic lipophilic balance) value of about 7 to 10. Most preferred is Neodol 23-3, with an HLB of about 8.

The level of nonionic emulsifier in gelled microemulsions of the invention suitably ranges from 10 to 40%, preferably from 15 to 35%, by weight based on total weight of the gelled microemulsion.

(b)(iii) Hair Styling Agent or Hair Conditioning Agent

The hydrophilic phase of the gelled water-in-oil microemulsion of the invention preferably comprises a hair styling agent or hair conditioning agent, most preferably a hair styling agent.

The hair styling agent can be a hair fixative or film former that imparts style-retention properties to hair, i.e., sets the hair.

Hair fixatives and film formers are typically polymeric in nature and many such polymers are available commercially which contain groups which render the polymers cationic, anionic, amphoteric or nonionic in nature (hereinafter referred to as "hair styling polymers").

Examples of suitable anionic hair styling polymers are:
copolymers of vinyl acetate and crotonic acid;
terpolymers of vinyl acetate, crotonic acid and a vinyl ester of an alpha-branched saturated aliphatic
monocarboxylic acid such as vinyl neodecanoate; copolymers of methyl vinyl ether and maleic anhydride (molar ratio about 1:1) wherein such copolymers are 50% esterified with a saturated alcohol containing from 1 to 4 carbon atoms such as ethanol or butanol; acrylic copolymers containing acrylic acid or methacrylic acid as the anionic radical-containing moiety with other monomers such as: esters of acrylic or methacrylic acid with one or more saturated alcohols having from 1 to 22 carbon atoms (such as methyl methacrylate, ethyl acrylate, ethyl methacrylate, n-butyl acrylate, t-butyl acrylate, t-butyl methacrylate, n-butyl methacrylate, n-hexyl acrylate, n-octyl acrylate, lauryl methacrylate and behenyl acrylate); glycols having from 1 to 6 carbon atoms (such as hydroxypropyl methacrylate and hydroxyethyl acrylate); styrene; vinyl caprolactam; vinyl acetate; acrylamide; alkyl acrylamides and methacrylamides having 1 to 8 carbon atoms in the alkyl group (such as methacrylamide, t-butyl acrylamide and n-octyl acrylamide);
and other compatible unsaturated monomers.
Specific examples of suitable anionic hair styling polymers are:
RESYN® 28-2930 available from National Starch (vinyl acetate/crotonic acid/vinyl neodecanoate copolymer);
Ultrahold® 8 available from BASF (CTFA designation Acrylates/acrylamide copolymer);

the Gantrez® ES series available from ISP corporation (esterified copolymers of methyl vinyl ether and maleic anhydride).

Other suitable anionic polymers include hydrophilically-modified polyurethanes. Examples of such materials are carboxylated polyurethanes, which are linear, hydroxyl-terminated copolymers having pendant carboxyl groups. They may be ethoxylated and/or propoxylated at least at one terminal end. The carboxyl group can be a carboxylic acid group or an ester group, wherein the alkyl moiety of the ester group contains one to three carbon atoms. The carboxylated polyurethane resin can also be a copolymer of polyvinylpyrrolidone and a polyurethane, having a CTFA designation PVP/polycarbamyl polyglycol ester. Suitable carboxylated polyurethane resins are disclosed in EP 0 619 111 A1 and U.S. Pat. No. 5,000,955. Other suitable hydrophilic polyurethanes are disclosed in U.S. Pat. Nos. 3,822,238; 4,156,066; 4,156,067; 4,255,550; and 4,743,673.

Examples of suitable amphoteric hair styling polymers are those containing cationic groups derived from monomers such as t-butyl aminoethyl methacrylate as well as carboxyl groups derived from monomers such as acrylic acid or methacrylic acid. One specific example of an amphoteric polymer is AMPHOMER (Octylacrylamide/acrylates/butylaminoethyl methacrylate copolymer) sold by the National Starch and Chemical Corporation.

Examples of suitable nonionic hair styling polymers are homopolymers of N-vinylpyrrolidone and copolymers of N-vinylpyrrolidone with compatible nonionic monomers such as vinyl acetate. Nonionic polymers containing N-vinylpyrrolidone in various weight average molecular weights are available commercially from ISP Corporation. Specific examples of such materials are homopolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

A preferred class of nonionic hair styling polymers are copolymers of vinylpyrrolidone with vinyl acetate such as those with tradenames LUVISKOL VA grades supplied by BASF Corporation, a most preferred polymer being LUVISKOL VA64 (PVA/VA 60/40).

Other suitable nonionic hair styling polymers are cross-linked silicone resins or gums. Specific examples include rigid silicone polymers such as those described in EP-A-240 350 and cross-linked silicone gums such as those described in WO 96/31188.

Examples of suitable cationic hair styling polymers are copolymers of amino-functional acrylate monomers such as lower alkyl aminoalkyl acrylate, or methacrylate monomers such as dimethylaminoethyl methacrylate, with compatible monomers such as N-vinylpyrrolidone, vinyl caprolactam, alkyl methacrylates (such as methyl methacrylate and ethyl methacrylate) and alkyl acrylates (such as ethyl acrylate and n-butyl acrylate).

Specific examples of suitable cationic hair styling polymers are:
copolymers of N-vinylpyrrolidone and dimethylaminoethyl methacrylate, available from ISP Corporation as Copolymer 845, Copolymer 937 and Copolymer 958;
copolymers of vinylpyrrolidone and dimethylaminopropylacrylamide or methacrylamide, available from ISP Corporation as Styleze CC10;
Polyquaternium-11 (formed by the reaction of diethyl sulphate and a copolymer of vinyl pyrrolidone and dimethyl aminoethylmethacrylate), available from ISP as Gafquat® 734, 755 and 755N, and from BASF as Luviquat® PQ11;
Polyquaternium-16 (formed from methylvinylimidazolium chloride and vinylpyrrolidone), available from BASF as Luviquat® FC 370, FC 550, FC 905 and HM-552;
Polyquaternium-46 (prepared by the reaction of vinylcaprolactam and vinylpyrrolidone with methylvinylimidazolium methosulphate), available from BASF as Luviquat®Hold.

With certain of the above-described hair styling polymers it may be necessary to neutralise some acidic groups to promote solubility/dispersibility. Examples of suitable neutralising agents include 2-amino-2-methyl-1,3-propanediol (AMPD); 2-amino-2-ethyl-1,3-propanediol (AEPD); 2-amino-2-methyl-1-propanol (AMP); 2-amino-1-butanol (AB); monoethanolamine (MEA); diethanolamine (DEA); triethanolamine (TEA); monoisopropanolamine (MIPA); diisopropanol-amine (DIPA); triisopropanolamine (TIPA); and dimethyl stearamine (DMS). A long chain amine neutralising agent such as lauramidopropyl dimethylamine may be employed, as is described in U.S. Pat. No. 4,874,604.

Another class of hair styling agent is a solid particulate material, which is able to impart body and stylability to the hair.

Preferred solid particulate materials have a D3,2 average particle size in the range from 10 to 700, preferably from 10 to 500, more preferably from 20 to 300, yet more preferably from 20 to 200, and most preferably from 30 to 150 nm, for example about from 50 to 100 nm.

It is preferred that the solid particulate materials be colloidal in an aqueous dispersion.

The solid particulate material can be a primary particle or an aggregate. Preferably, it is a primary particle.

Suitably, the solid particles are relatively hard and typically have a Youngs Modulus of more than 0.01, preferably more than 0.1, more preferably more than 1.0, yet more preferably more than 4 GPa, and yet more preferably more than 10 GPa.

The solid particulate materials can be organic or inorganic in nature. Furthermore, the solid particulate material may be composed entirely of one material or may consist of a composite of materials.

Examples of suitable solid particulate materials include polymers, which are preferably cross-linked, (e.g. polystyrene, silicone elastomer powders, PTFE, rubber), silicas, alumina, aluminosilicate, clays and colloidal metals (e.g. titanium dioxide, zinc oxide).

A preferred class of solid particulate materials are silicas, such as silica gels, hydrated silicas and precipitated silicas (e.g. Cab-O-Sil and Aerosil, from Cabot Corp. and Degussa respectively).

A particularly preferred class of silicas are the colloidal silicas. Suitable examples include Ludox HS-40, Ludox TM-40, Ludox SM, Ludox CL and Ludox AM (from Grace Davison Products).

Mixtures of any of the above described hair styling agents may also be used.

The total amount of hair styling agent suitably ranges from 0.05 to 5%, preferably from 0.5 to 2%, by weight based on total weight of the gelled microemulsion.

One suitable class of conditioning agent is a quaternary ammonium cationic surfactant.

Examples of suitable cationic surfactants of this type are those corresponding to the general formula:

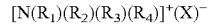

in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms;

and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

Preferred cationic surfactants are monoalkyl quaternary ammonium compounds in which the alkyl chain length is C12 to C22.

Other preferred cationic surfactants are so-called dialkyl quaternary ammonium compounds in which R1 and R2 independently have an alkyl chain lengths from C12 to C22 and R3 and R4 have 2 or less carbon atoms.

Examples of suitable cationic surfactants include: cetyltrimethylammonium chloride, behenyltrimethylammonium chloride, cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, PEG-2 oleylammonium chloride and salts of these where the chloride is replaced by other halogen, (e.g. bromide), acetate, citrate, lactate, glycolate, phosphate nitrate, sulphate, or alkylsulphate. Other suitable cationic surfactants include those materials having the CTFA designations Quaternium-5, Quaternium-31 and Quaternium-18.

Preferred examples are cetyltrimethylammonium chloride, available commercially, for example as ARQUAD 16/29, from Akzo, and lauryl trimethylammonium chloride, available commercially, for example as ARQUAD C-35, from Akzo.

Another suitable class of conditioning agent is a cationic polymer.

By "cationic polymer" is meant any polymer containing cationic groups and/or groups that can be ionized into cationic groups.

Suitable cationic polymers may be homopolymers or may be formed from two or more types of monomers.

The weight average ($M_w$) molecular weight of the cationic polymer is preferably between 300,000 and 2M Dalton, more preferably between 750,000 and 1.5M Dalton.

The cationic groups will generally be present as a substituent on a fraction of the total monomers of the cationic polymer. Thus when the polymer is not a homopolymer it can contain non-cationic spacer monomers. Such polymers are described in the CTFA Cosmetic Ingredient Dictionary, 3rd edition. The ratio of the cationic to non-cationic monomers is selected to give polymers having a cationic charge density in the required range.

The cationic charge density of the cationic polymer may suitably be determined via the Kjeldahl method as described in the US Pharmacopoeia under chemical tests for nitrogen determination. Preferred cationic polymers will have cationic charge densities of at least about 0.9 meq/gm, more preferably at least about 1.6 meq/gm, most preferably at least about 1.8 meq/g, but also preferably less than about 7 meq/gm, more preferably less than about 5 meq/gm, most preferably less than about 3.0 meq/g, as measured at the pH of intended use of the microemulsion. The pH of intended use of the microemulsion typically ranges from about pH 3 to about pH9, preferably from about pH4 to about pH7.

Any anionic counterions may be use in association with the cationic polymers so long as the cationic polymers remain soluble in the hydrophilic phase, and so long as the counterions are physically and chemically compatible with the essential components of the microemulsion or do not otherwise unduly impair product performance, stability or aesthetics. Examples of such counterions include: halides (e.g., chloride, fluoride, bromide, iodide), sulfate, methylsulfate, and mixtures thereof.

The preferred cationic polymers are chosen from those that contain units comprising primary, secondary, tertiary and/or quaternary amine groups that can either form part of the main polymer chain or can be borne by a side substituent directly connected thereto.

Suitable cationic polymers may be naturally-derived materials such as cationic polysaccharides.

Cationic polysaccharides suitable for use in compositions of the invention include monomers of the formula:

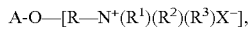

wherein: A is an anhydroglucose residual group, such as a starch or cellulose anhydroglucose residual. R is an alkylene, oxyalkylene, polyoxyalkylene, or hydroxyalkylene group, or combination thereof. $R^1$, $R^2$ and $R^3$ independently represent alkyl, aryl, alkylaryl, arylalkyl, alkoxyalkyl, or alkoxyaryl groups, each group containing up to about 18 carbon atoms. The total number of carbon atoms for each cationic moiety (i.e., the sum of carbon atoms in $R^1$, $R^2$ and $R^3$) is preferably about 20 or less, and X is an anionic counterion.

Preferred cationic polysaccharides are cationic cellulose derivatives such as those salts of hydroxyethyl cellulose reacted with trimethyl ammonium substituted epoxide, referred to in the industry (CTFA) as Polyquaternium 10. Specific examples of these materials include those polymers available from Amerchol Corporation in their Polymer JR series of polymers, such as Polymer JR125, Polymer JR400 and Polymer JR30M. Other suitable types of cationic cellulose include the polymeric quaternary ammonium salts of hydroxyethyl cellulose reacted with lauryl dimethyl ammonium-substituted epoxide referred to in the industry (CTFA) as Polyquaternium 24.

Another preferred class of cationic polysaccharide that can be used is a cationic guar gum derivative, especially guar hydroxypropyltrimethylammonium chloride. Specific examples of these materials include those polymers available from Rhodia in their JAGUAR series of polymers, such as JAGUAR C13S and JAGUAR C17.

Suitable cationic polymers may also be synthetically-derived materials such as those formed from vinyl monomers having cationic amine or quaternary ammonium functionalities, optionally together with non-cationic spacer monomers.

Suitable non-cationic spacer monomers include (meth) acrylamide, alkyl and dialkyl (meth)acrylamides, alkyl (meth)acrylate, vinyl caprolactone and vinyl pyrrolidine. The alkyl and dialkyl substituted monomers preferably have C1-C7 alkyl groups, more preferably C1-3 alkyl groups. Other suitable water soluble spacer monomers include vinyl esters, vinyl alcohol, maleic anhydride, propylene glycol and ethylene glycol.

Suitable vinyl monomers having cationic amine or quaternary ammonium functionalities include dialkylaminoalkyl acrylate, dialkylaminoalkyl methacrylate, dialkylaminoalkyl acrylamide, dialkylaminoalkyl methacrylamide, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidone, e.g., alkyl vinyl imidazolium, alkyl vinyl pyridinium, alkyl vinyl pyrrolidone salts. The alkyl portions of these monomers are preferably lower alkyls such as the C1, C2 or C3 alkyls.

Examples of suitable cationic polymers formed from the above types of monomer include copolymers of 1-vinyl-2-pyrrolidone and 1-vinyl-3-methylimidazolium salt (e.g. chloride salt) (referred to in the industry by the Cosmetic, Toiletry, and Fragrance Association, "CTFA", as Polyquaternium-16); copolymers of 1-vinyl-2-pyrrolidone and dimethylaminoethyl methacrylate (referred to in the industry by CTFA as Polyquaternium-11); cationic diallyl quaternary ammonium-containing polymers, including, for example, dimethyldiallylammonium chloride homopolymer, copolymers of acrylamide and dimethyldiallylammonium chloride (referred to in the industry by CTFA as Polyquaternium 6 and Polyquaternium 7, respectively); terpolymers of acrylic acid with dimethyldiallylammonium chloride and acrylamide (referred to in the industry by CTFA as Polyquaternium 39), and terpolymers of acrylic acid with methacrylamidopropyl trimethylammonium chloride and methyl acrylate (referred to in the industry by CTFA as Polyquaternium 47).

Mixtures of any of the above described hair conditioning agents may also be used.

The total amount of hair conditioning agent suitably ranges from 0.05 to 4%, preferably from 0.07 to 3%, by weight based on total weight of the gelled microemulsion.

(c) Gelling Agent

The gelled water-in-oil microemulsion of the invention comprises a gelling agent.

The gelling agent may suitably be any material or mixture of materials that may be dissolved or dispersed into the oil phase (a) at elevated temperature (e.g. greater than 50° C.) to form a homogeneous solution or dispersion and which will substantially thicken or harden the oil phase (a) upon cooling to form a gel at room temperature (about 25° C.).

Suitable gelling agents include esters and amides of fatty acid gellants, hydroxy acids, hydroxy fatty acids, cholesterolic materials, lanolinolic materials, other amide gellants, crystalline gellants.

Preferred are N-acyl amino acid amides prepared from glutamic acid, lysine, glutamine, aspartic acid and mixtures thereof.

Particularly preferred are n-acyl glutamic acid amides corresponding to the following formula:

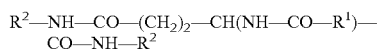

in which $R^1$ is an aliphatic hydrocarbon radical having from about 12 to about 22 carbon atoms, and $R^2$ is an aliphatic hydrocarbon radical having from about 4 to about 12 carbon atoms. Examples of these include n-lauroyl-L-glutamic acid dibutyl amide, n-stearoyl-L-glutamic acid diheptyl amide, and mixtures thereof. Most preferred is n-lauroyl-L-glutamic acid dibutyl amide, also referred to as dibutyl lauroyl glutamide. This material is commercially available with tradename Gelling agent GP-1 available from Ajinomoto.

The total amount of gelling agent suitably ranges from 0.1 to 3%, preferably from 0.5 to 1.5%, by weight based on total weight of the gelled microemulsion.

Process

A suitable process for preparing a water-in-oil gelled microemulsion according to the present invention comprises the following steps:

(I) dissolving or dispersing the gelling agent (c) in a portion of the oil phase [(a)];
(II) in a separate vessel, forming a water-in-oil microemulsion by mixing the remaining oil phase [(a)], the water [(b)(i)], and the nonionic emulsifier;
(III) blending the solution or dispersion obtained in (I) with the water-in-oil microemulsion obtained in (II), to form a water-in-oil gelled microemulsion.

A preferred process for preparing a water-in-oil gelled microemulsion according to the present invention comprises the following steps:

(I) dissolving or dispersing the gelling agent (c) in a portion of the oil phase [(a)];
(II) in a separate vessel, forming a solution or dispersion of styling agent [(b)(iii)] in the water [(b)(i)];
(III) in a separate vessel, forming a water-in-oil microemulsion by mixing the remaining oil phase [(a)], the water [(b)(i)], the solution or dispersion obtained in (II), and the nonionic emulsifier [(b)(ii)], and
(IV) blending the solution or dispersion obtained in (I) with the water-in-oil microemulsion obtained in (III), to form a water-in-oil gelled microemulsion with styling agent.

Product Form and Usage

Compositions of this invention are preferably for application directly to the hair in neat form, either before or after shampooing.

Accordingly the invention also provides a method of treating hair comprising the step of applying a gelled water-in-oil microemulsion as described above directly to the hair as a pre-wash treatment or as a post-wash treatment.

Optional Ingredients

Compositions of this invention may contain any other ingredient normally used in hair treatment formulations. These other ingredients may include preservatives such as Phenoxetol® (2-phenoxyethanol), colouring agents, antioxidants such as BHT (butylhydroxytoluene), fragrances and antimicrobials such as Glycacil-L® (iodopropynyl butylcarbamate). Each of these ingredients will be present in an amount effective to accomplish its purpose. Generally these optional ingredients are included individually at a level of up to about 5% by weight based on total weight of the gelled microemulsion.

The invention is further illustrated by way of the following Examples, in which all percentages are by weight based on total weight unless otherwise stated.

EXAMPLES

Example 1

A gelled water-in-oil microemulsion was prepared having ingredients as shown in the following Table:

| Ingredient | Example 1 |
| --- | --- |
| Sunflower oil | 32.0 |
| Light mineral oil (Sirius M40, from Silkolene) | 32.0 |
| Nonionic emulsifier (NEODOL 23-3, from Shell Co.) | 30.0 |
| Water | to 100 |
| Gelling agent (GP-1 from Ajinomoto) | 1.0 |
| Phenoxetol (from Clariant) | 0.4 |
| BHT | 0.05 |
| Glycacil-L (from Lonza) | 0.1 |
| Perfume | 0.15 |

The preparation process was as follows:
A. Dissolve the Phenoxetol, BHT and Glycacil-L in half of the sunflower oil. Add the M40, the Neodol 23-3, and the water and heat to 50° C.
B. In a separate vessel, add the GP-1 to the remaining sunflower oil and heat whilst gently stirring until the GP-1 dissolves (145-150° C.)
C. When the temperature of water-in-oil microemulsion A has fallen to about 90° C., add solution B (50° C.)
D. Continue gentle stirring of mixture C and add perfume below 40° C.

Example 2

A gelled water-in-oil microemulsion with styling agent was prepared having ingredients as shown in the following Table:

| Ingredient | Example 2 |
| --- | --- |
| Sunflower oil | 31.4 |
| Light mineral oil (Sirius M40, from Silkolene) | 31.4 |
| Nonionic emulsifier (NEODOL 23-3, from Shell Co.) | 30.0 |
| Water | to 100 |
| Styling agent (LUVISKOL VA64, from BASF) | 1.2 |
| Gelling agent (GP-1 from Ajinomoto) | 1.0 |
| Phenoxetol (from Clariant) | 0.4 |
| BHT | 0.05 |
| Glycacil-L (from Lonza) | 0.1 |
| Perfume | 0.15 |

The preparation process was as follows:
A. Dissolve the Luviskol in the water. In a separate vessel, dissolve the Phenoxetol, BHT and Glycacil-L in half of the sunflower oil. Add the M40, the Neodol 23-3E, and the Luviskol solution and heat to 50° C.
B. In a separate vessel, add the GP-1 to the remaining sunflower oil and heat whilst gently stirring until the GP-1 dissolves (145-150° C.).
C. When the temperature of water-in-oil microemulsion A has fallen to about 90° C., add solution B (50° C.).
D. Continue gentle stirring of mixture C and add perfume below 40° C.

Comparative Example A

A gelled oil (not according to the invention) was prepared having ingredients as shown in the following Table:

| Ingredient | Comparative Example A |
| --- | --- |
| Sunflower oil | 46.65 |
| Light mineral oil (Sirius M40, from Silkolene) | 46.65 |
| Nonionic emulsifier (NEODOL 23-3, from Shell Co.) | 5.0 |
| Gelling agent (GP-1 from Ajinomoto) | 1.0 |
| Phenoxetol (from Clariant) | 0.4 |
| BHT | 0.05 |
| Glycacil-L (from Lonza) | 0.1 |
| Perfume | 0.15 |

The preparation process was as follows:
A. Dissolve the Phenoxetol, BHT and Glycacil-L in half of the sunflower oil. Add the M40 and heat to 50° C.
B. In a separate vessel, add the GP-1 to the remaining sunflower oil heat whilst gently stirring until the GP-1 dissolves (145-150° C.). Remove heat and immediately add all the Neodol 23-3E (Neodol at room temperature, oil at 145° C.). Continue gentle stirring.
C. When the temperature of solution A has fallen to about 90° C., add mixture B (50° C.).
D. Continue gentle stirring of mixture C and add perfume below 40° C.

Rheology Evaluations

FIG. 1 shows the results of controlled stress rheometry testing on the following formulations:
(a) The formulation of Example 1 (indicated as "microemulsion gel" on the graph)
(b) The formulation of Comparative Example A (indicated as "oil gel" on the graph)
(c) A control formulation (Comparative Example B) of 50 wt % Sirius M40 and 50 wt % sunflower oil (indicated as "oil" on the graph)
(d) A control formulation (Comparative Example C) which is a non-gelled water-in-oil microemulsion containing 32.5 wt % Sirius M40, 32.5 wt sunflower oil, 30 wt % Neodol 23-3, and balance water (indicated as "non-gelled microemulsion" on the graph).

The rheology profile reveals that both "oil" (Comparative Example B) and "non-gelled microemulsion" (Comparative Example C) are Newtonian liquids. "Oil gel" (Comparative Example A) has higher viscosity at zero shear than "oil" (Comparative Example B) and is non-Newtonian. However, "microemulsion gel" (Example 1) has a higher viscosity at zero shear and a higher and sharper critical yield stress as compared to "oil gel" (Comparative Example A)

Performance Evaluations

The formulation of Example 1 was compared against the formulation of Comparative Example C across a number of performance attributes. Evaluation was carried out in two stages:
(i) Post treatment.
Half of the hair of a mannequin head was treated with the formulation of Example 1 and the other half with the formulation of Comparative Example C. 2.0 ml of formulation was used to treat the individual half head. After one hour the mannequin head was assessed by an expert salon hairdresser.
(ii) Post wash.
3.5 ml of a commercial shampoo was measured and applied onto the treated half head, followed by washing and rinsing in accordance with normal procedures. The shampooing and rinsing procedure was repeated for a second application. The same procedure was followed for the other treated half head. After washing and rinsing was complete the mannequin head was allowed to dry at normal temperature (20 to 25 degrees C.). On drying the mannequin head was assessed by an expert salon hairdresser.

The following results were obtained:

Post treatment:
Compared to Comparative Example C, the formulation of Example 1 gave significantly (>99%) better hair body, significantly (>95%) better hair conditioning, significantly (>90%) better hair shine and significantly (>90%) reduced hair sticky feel.

Post wash:
Compared to Comparative Example C, the formulation of Example 1 gave significantly (>90%) better hair shine.

The formulation of Example 1 was also compared against the formulation of Comparative Example B for post wash performance attributes, using a similar test protocol to that described above.

Compared to Comparative Example B, the formulation of Example 1 gave significantly (>99%) better post-wash hair softness and significantly (>99%) better post-wash hair gloss.

To demonstrate the added benefits of incorporating styling agent, the formulation of Example 1 was compared against the formulation of Example 2, using a similar test protocol to that described above.

The following results were obtained:
Post treatment:
Compared to Example 1, the formulation of Example 2 gave significantly (>99%) better hair body.
Post wash:
Compared to Example 1, the formulation of Example 2 gave significantly (>95%) better hair conditioning and significantly (>90%) better hair shine.

Stability Evaluations

In a further test, the "oil gel" (Comparative Example A) was blended directly with a solution of styling agent (LUVISKOL VA64 at the same weight percentage (1.2%) to that in Example 2). This resulted in an unstable formulation in which water droplets from the polymer solution settled at the bottom of the storage jar immediately. By contrast, the formulation of Example 2 remained stable on storage for over 6 months at 25 degrees C.

The invention claimed is:

1. A gelled water-in-oil microemulsion for hair treatment comprising:
   (a) an oil phase comprising:
   (i) 10 to 95% by wt. based on total weight of the gelled microemulsion of a first oily component which is one or more glyceride fatty esters, and
   (ii) 5 to 95% by wt. based on total weight of the gelled microemulsion of a second oily component which is one or more hydrocarbon oils of average carbon chain length less than 20 carbon atoms;
   (b) a hydrophilic phase comprising:
   (i) about 2 to 10% by wt. based on total weight of the gelled microemulsion of water,
   (ii) a nonionic emulsifier which is an ethoxylated alcohol having an HLB of at least 6, and
   (iii) 0.05 to 4% by wt. of a hair styling agent or hair conditioning agent based on total weight of the gelled microemulsion, and
   (c) 0.1 to 3% by wt. based on total weight of the gelled microemulsion of a gelling agent, wherein said gelling agent is an n-acyl glutmic acid amide corresponding to the following formula:

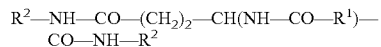

in which $R^1$ is an aliphatic hydrocarbon radical having from 12 to 22 carbon atoms, and $R^2$ is an aliphatic hydrocarbon radical having from 4 to 12 carbon atoms.

2. A gelled microemulsion according to claim 1, in which the source of glyceride fatty esters is selected from coconut oil, sunflower oil, almond oil and mixtures thereof.

3. A gelled microemulsion according to claim 1, in which the total content of glyceride fatty ester ranges from 20% to 80% by weight based on total weight of the gelled microemulsion.

4. A gelled microemulsion according to claim 1, in which the hydrocarbon oil is light mineral oil.

5. A gelled microemulsion according to claim 1, in which the total content of hydrocarbon oil ranges from 20% to 80% by weight based on total weight of the gelled microemulsion.

6. A gelled microemulsion according to claim 1, in which the glyceride fatty ester hydrocarbon oil weight ratio ranges from 95:5 to 5:95, preferably from 90:10 to 10:90, most preferably from 80:20 to 20:80.

7. A gelled microemulsion according to claim 1, in which the water level ranges from 3 to 7% by weight based on total weight of the gelled microemulsion.

8. A gelled microemulsion according to clam 1, in which the HLB value of the ethoxylated alcohol ranges from 6 to 12.

9. A gelled microemulsion according to claim 8, in which the ethoxylated alcohol is a higher aliphatic, primary alcohol containing about 9 to 15 carbon atoms, condensed with about 2.5 to 10 moles of ethylene oxide.

10. A gelled microemulsion according to claim 9, in which the ethoxylated alcohol is C12 to 13 alkanol condensed with 3 moles ethylene oxide.

11. A gelled microemulsion according to claim , which comprises a hair styling agent which is a hair fixative or film former.

12. A gelled microemulsion according to claim 11, in which the hair fixative or film former is a copolymer of vinylpyrrolidone with vinyl acetate.

13. A gelled microemulsion according to claim 1 in which the gelling agent is n-lauroyl-L-glutamic acid dibutyl amide.

14. A method of treating hair comprising the step of applying a gelled water-in-oil microemulsion according to claim 1 directly to the hair as a pre-wash treatment or as a post-wash treatment.

* * * * *